United States Patent [19]

Marshall et al.

[11] Patent Number: 4,921,659
[45] Date of Patent: May 1, 1990

[54] METHOD OF FORMING A FIBROUS WEB USING A VARIABLE TRANSVERSE WEBBER

[75] Inventors: Gerald M. Marshall, Somerville; Allan P. Farrington, Englishtown, both of N.J.

[73] Assignee: Chicopee, New Brunswick, N.J.

[21] Appl. No.: 297,728

[22] Filed: Jan. 17, 1989

Related U.S. Application Data

[62] Division of Ser. No. 99,877, Sep. 22, 1987.

[51] Int. Cl.⁵ ............................................. D04H 1/72
[52] U.S. Cl. ................................. 264/510; 264/518; 264/113; 264/116; 425/81.1
[58] Field of Search ............... 264/510, 511, 512, 517, 264/518, 113, 115, 116, 121; 425/80.1, 81.1, 82.1, 83.1

[56] References Cited

U.S. PATENT DOCUMENTS

| | | | |
|---|---|---|---|
| 3,512,218 | 5/1970 | Langdon | 425/82.1 |
| 3,535,187 | 10/1970 | Wood | 425/82.1 |
| 3,740,797 | 6/1973 | Farrington | 425/82.1 |
| 3,768,118 | 10/1973 | Ruffo et al. | 264/518 |
| 3,772,739 | 11/1973 | Lovgren | 425/82.1 |
| 3,895,089 | 7/1975 | Goyal | 264/518 |
| 3,914,080 | 10/1975 | Kamp | 425/83.1 |
| 4,166,090 | 8/1979 | Green et al. | 264/113 |
| 4,724,114 | 2/1988 | McFarland et al. | 264/510 |
| 4,767,586 | 8/1988 | Radwanski et al. | 264/113 |

Primary Examiner—Jan H. Silbaugh
Assistant Examiner—MaryLynn Fertig
Attorney, Agent, or Firm—Joseph F. Shirtz

[57] ABSTRACT

A web or structure is formed by feeding separate supplies of fibrous material into contact with two separate lickerins that are parallel to each other and rotated toward each other. The fibers from the two lickerins pass through a mixing zone and are accumulated on a moving conveying screen that is moved parallel to the axes of the lickerins. Segmented baffle plates may be inserted into the mixing zone to control the lateral or cross-sectional composition of a web formed by the fibers accumulated on the screen. A segmented feed may be used to advantageously deliver different fiber materials at different rates to each lickerin. Radially layered composite web structures having circular cross-sections may be formed with the same apparatus by forming the conveying screen into a U-shape and selectively controlling the air flow through the screen.

9 Claims, 7 Drawing Sheets

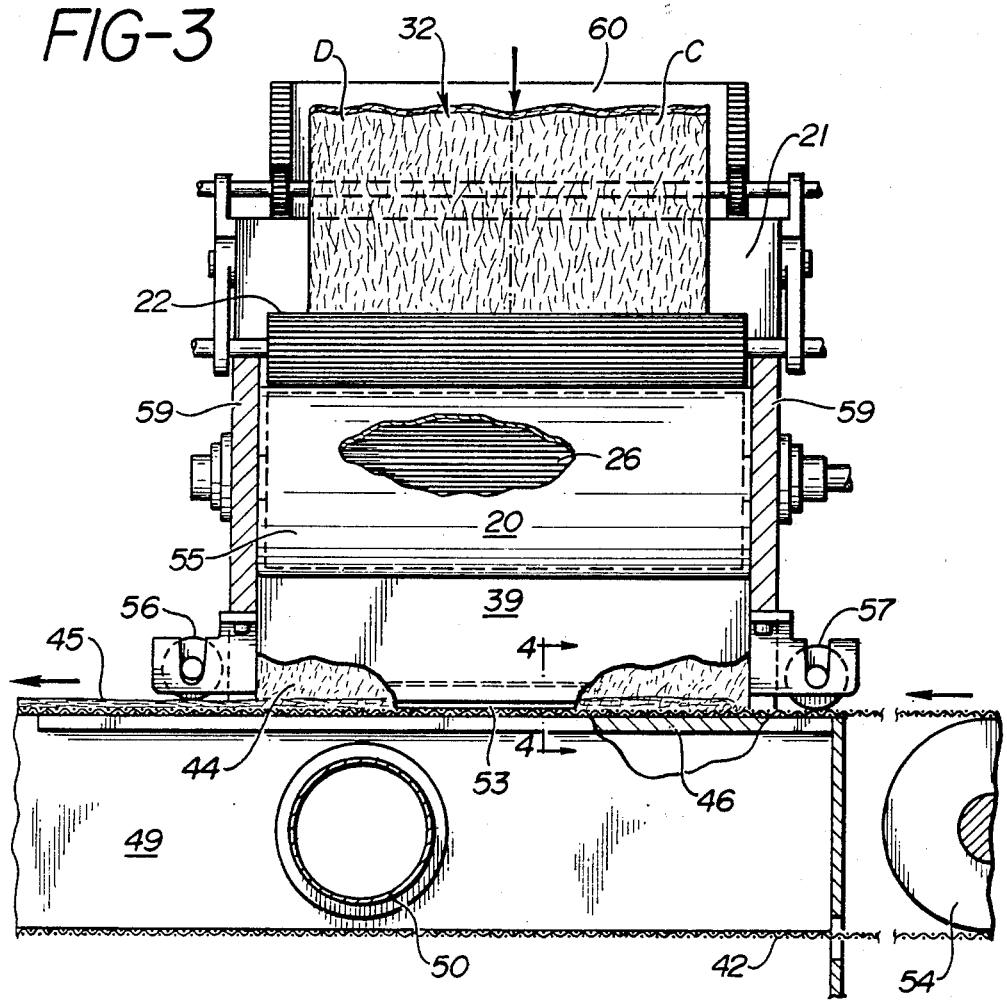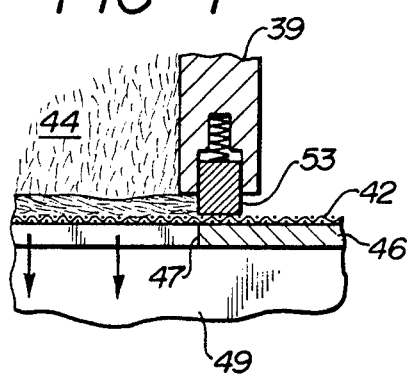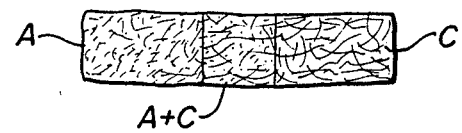

METHOD OF FORMING A FIBROUS WEB USING A VARIABLE TRANSVERSE WEBBER

This is a division of application Ser. No. 99,877, filed Sept. 22, 1987.

TECHNICAL FIELD

This invention relates to an improved method and apparatus for forming nonwoven structures consisting of a more or less uniform intermixture of randomly oriented fibers obtained from separate supplies of individualized fibers, such as textile and paper-making fibers.

BACKGROUND OF THE INVENTION

Nonwoven fiber structures frequently consist of a random yet homogeneous agglomeration of long and short fibers. Long fibers are fibers of both natural and synthetic origin that are suitable for textiles. They are longer than 0.25 inches and generally range between 0.5 and 2.5 inches in length. Short fibers are suitable for paper-making and are generally less than about 0.25 inches long, such as wood pulp fibers or cotton linters. It is known in the art that strong nonwoven structures can be made by rapidly and reliably blending inexpensive short fibers with strong long fibers.

Random distribution of the blended fibers results in an isotropic web or structure that is uniformly strong in all directions. The fibers can also be directionally disposed or aligned, resulting in an anisotropic fabric that is strong in the direction of alignment. Nonwoven fabrics are less costly than woven or knitted material, yet are more or less comparable in physical properties, appearance, and weight. Thus, inexpensive nonwoven fabrics are available for a wide variety of products, including, hand towels, table napkins, sanitary napkins, hospital clothing, draperies, cosmetic pads, etc. These nonwoven webs can be particularly advantageous when formed as a layered or composite structure having selective absorbent properties.

The desired utility and characteristics of the nonwoven end product dictate the types of fibers and the relative proportions of long and short fibers in a web. The desired characteristics may include, for example, tear resistance, abrasion resistance, stretchability, strength, absorption or non-absorption to different liquids, heat sealability, and resistance to delamination. Thus, a strong yet absorbent web may advantageously be formed from two or more long and short fibers, such as rayon and wood pulp combined in varying percentages.

There are many different methods and devices useful for making nonwoven webs and other fibrous structures. Conventional carding or garnetting methods produce nonwoven fiber webs, but these are generally and are limited to textile length fibers.

The "Rando-Webber" process may be used to make nonwoven webs. In this process, pre-opened textile fiber material is delivered to a lickerin that opens the fibers further, and introduces them to a high-velocity low-pressure air stream. The fibers are randomly deposited on a condensing screen to form an isotropic web. While a uniform web of textile fibers can be obtained, this process is not suitable for use with short fibers or blends of long and short fibers.

U.S. Pat. No. 3,512,218 of Langdon describes two lickerins and rotary feed condenser assemblies arranged in parallel one after the other. Isotropic nonwoven webs are formed with this apparatus by feeding fibrous material to the lickerins, where the fibers are individualized and deposited on a condenser screen. A single airstream is divided into two parts and acts to doff the fibers from the lickerins and deposit them onto the screen, where the web is formed. This method cannot be used to homogeneously blend two streams of fibers.

In U.S. Pat. No. 3,535,187 of Woods there is described apparatus for producing a layered web of randomly oriented fibers joined at the interface of adjacent layers by a small zone of textile length fibers extending across the interface. Wood's device provides individualized fibers which are deposited on a pair of cylindrical condenser screens by a pair of respective lickerins acting in cooperation with high-speed, turbulent air streams that move faster than the lickerin in order to doff the fibers. However, the air speed must also be controlled so that the fibers do not forcibly impact on the condensers. The condenser screens are positioned closely adjacent to one another and the layers of fibers on the condensers are compressed between the condensers to form a composite nonwoven web with some blending at the interface between layers. However, there is no substantial fiber mixing zone adjacent to the condensers, and the intermixing of fibers is minimal.

One way of making a nonwoven web consisting of a mixture of randomly oriented long and short fibers uses a milling device to individualize short fibers and a lickerin to individualize long fibers. The fibers are mixed in a mixing zone, and the mixture is deposited on a condenser to form a nonwoven web. Though randomly oriented, the mixed fibers are stratified rather than homogeneously blended. The long fibers predominate on one side of the web and the short fibers predominate on the other. In addition, undesirable clumps of fibers or "salt" occur in this web product, because the mill does not completely individualize the short wood pulp fibers.

Another method used to make webs of mixed and randomly oriented long and short fibers introduces pre-opened long and short fibers to a single lickerin for individualization. However, the optimum lickerin speeds for long and short fibers are different. To prevent the degradation of long fibers, this device must operate at the slower speed that is optimum for long fibers. As a result, the speed and throughput of the device is compromised.

Methods and devices which produce a blend of long and short fibers without clumps or salt are disclosed in U.S. Pat. No. 3,772,739 of Lovgren. Lovgren provides for the separate and simultaneous individualization of each type of fiber on separate lickerins, each operating at an optimum speed for the fiber it opens. For example, long fibers such as rayon are supplied to a lickerin operating in the neighborhood of 2400 rpm. Pulpboard is supplied to a lickerin operating in the neighborhood of 6000 rpm, a speed that would damage long fibers. The fibers are doffed from their respective lickerins by separate air streams and are entrained in the separate air streams. These streams are subsequently mixed in a mixing zone in order to blend the fibers. The homogeneous blend is then deposited in a random fashion on a condenser disposed in proximity to the mixing zone. While the Lovgren apparatus is useful, it does not lend itself to the preparation of a wide variety of webs.

Another method of producing homogeneous blends of fibers is disclosed in commonly owned U.S. Pat. No. 3,740,797 of Farrington. Farrington discloses a method and machine wherein supplies of fibers are fed to oppositely rotating parallel lickerins, which are operated at respective optimum speeds to produce individualized long and short fibers. The individualized fibers are doffed from the lickerins by centrifugal force and by high velocity air streams directed against any fibers tending to cling to the lickerin structure. The individualized fibers from each supply are entrained in their respective air streams and are impelled toward each other at high velocities along trajectories that intersect in a mixing zone, where at least a portion of the fibers from each supply may be blended. A condensing means or screen with a vacuum chamber below it communicates with the mixing zone so that the blended fibers are deposited on the condenser screen within a condensing zone so as to produce an isotropic web of fibers. This screen is moved in a direction, i.e. the "machine direction," which is perpendicular to the axis of the lickerins. In addition, a baffle can be interposed between the air streams to control the degree of mixing and the respective location of the long and short fibers in the composite web.

Farrington provides a method and apparatus for producing an air laid nonwoven web of homogeneously blended and randomly oriented short and long fibers that is isotropically strong and is free of salt. While Farrington provides for a wide variety of nonwoven web products, that process is still insufficient to produce many desirable nonwoven structures or webs.

It is known to form cylindrical nonwoven web structures, such as tampon-type sanitary products. This is accomplished by necking down a carded web of material into a sliver. The sliver is cut into sections which are rolled into a cylindrical shape, and then compressed. This process has limitations in terms of the speed at which the product is created.

Thus it would be advantageous to provide a method and apparatus for making thicker webs more rapidly than with the Farrington process, and webs having a wider range of shapes and composite structures than can be made on known machines by known methods.

SUMMARY OF THE INVENTION

The present invention is directed to the high-speed production of blends of long and short fibers that result in a wide variety of composite nonwoven web structures of different widths, thicknesses, shapes and compositions.

In an illustrative embodiment of the invention two independent fiber sources driven by feed rolls are individualized by parallel counter-rotating lickerins. The individualized fibers are doffed from the lickerins by air streams and centrifugal force, and are carried to a mixing zone. The fibers may be randomly and uniformly mixed in the zone or may be segregated by type, and then directed to a condensing zone where they are deposited onto a narrow condensing screen which is located in the condensing zone. The mixing zone is below the parallel lickerins and is defined generally by the space between the lickerins and the condensing zone, which is below the mixing zone. The screen is moved parallel to the axes of the lickerins, which is transverse to the conventional orientation. The motion of the screen with respect to the lickerins and the frame which houses them defines an input or rear end of the condensing zone, where the screen first enters the condensing zone and receives individualized fibers, and an exit or front end, where the formed web ceases to receive fibers and is expelled from communication with the condensing zone. At any given moment during operation of the apparatus, the web is formed in the condensing zone between the input and exit ends, which also generally define the operating length of the lickerins.

Duct plates are used to additionally define a path between the lickerins and the condenser screen, and a vacuum chamber with a slot located below the screen is preferably used to form the air streams that doff the fibers from the lickerins and help deposit the fibers onto the screen. Since the screen travels parallel to and between the lickerins axes, there is a high-speed transverse formation of a web of nonwoven fibers. The transverse webber according to the invention provides a long web formation zone whose length is limited only by the practical length of the lickerins and whose width is limited only by the practical duct configuration between the lickerins and the screen.

Composite and layered structures can be made by varying the material introduced to the lickerins along the length of each lickerin. Webs having different cross-sectional shapes can be generated by varying the configuration of the duct plates or the vacuum slot in the condensing zone, by introducing baffles into the mixing zone, or by programmably driving the feed rolls, or combinations thereof. In one embodiment, the condenser screen can be progressively curved, so that the web is given a form as it is condensed, rather than in a subsequent operation.

According to the invention, separate sources of short and long fibers, such as pulp and rayon, respectively, are individualized by separate lickerins and formed into a web. Each fiber source is guided by feed rolls and a nose bar into engagement with its lickerin, and each lickerin is rotated at a high speed that is suitable for the fibers it is acting on. The two lickerins are parallel to each other and rotate toward each other, i.e. in opposite directions. The nose bar and lickerin are arranged to provide a fiberizing station having the optimum opening relationship for the fibers. Each lickerin acts on its fiber supply and rapidly individualizes the fibers through violent contact between the fiber supply and the rapidly rotating teeth of the lickerin.

The counter-rotating lickerins create a centrifugal force that tends to tangentially throw the individual fibers from each lickerin toward the fibers from the other lickerin. Gravity, an air stream naturally generated by the rotation of each lickerin, and the high speed air stream created by a suction force below the condenser screen tend to impel the tangentially thrown fibers from the lickerin downward and toward each other. These tangential and downward vector components carry the individualized fibers to a centrally disposed mixing zone between, but below, the lickerins.

The stream of individual fibers entering the mixing zone from the two lickerins are dilute, allowing the two streams to intersect each other, such that the fibers cross each other without a substantial number of collisions. As a result, the fibers from the lickerin to the left of the condenser screen tend to reach predominately the right side of the screen and visa versa.

A different mixing pattern of the fibers can be accomplished by inserting a baffle into the mixing zone between the lickerins. This baffle intersects part of each stream of fibers and deflects it back in the opposite direction, such that the long and short fibers are spread across the lateral width of the web. This results in a proportionally uniform mixing of the long and short fibers across the web. If the baffle completely intersects the streams, the material from the lickerin on the left is reflected back to the left and vise versa, so that a product with a distribution essentially opposite that with no baffle is created. Therefore, the present invention produces products which may have different compositions than in the prior art, for example, webs formed in laterally separated strips.

The deposition of fibers occurs as the condenser screen moves along the length of the lickerins, e.g. 40 inches. Thus for the same screen speed and feed rate, the material deposited per inch of screen width is greater than in the prior art wherein the lickerin axes are perpendicular to the screen movement direction and the condensing zone is only the separation between the ducts extending from the lickerins, i.e. about 4 inches.

The width of the web is determined, according to the invention, by the distance between the lickerins, if parallel ducts are used. However, the duct may diverge from the lickerins to the condensing zone. In such a case the width is determined by the angle of divergence and the distance from the lickerins to the screen, which are in turn limited by the ability of the fiber/air stream to expand while maintaining a uniform flow profile without separation from the duct walls. When the condenser screen is in the form of an endless moving belt, the length of the web is generally continuous, unless and until the supply of fiber is exhausted. The thickness and density of the web is determined primarily by the fibers chosen, the proportion at which they are mixed, the feed roller speed, and the rate at which the condensing screen is moved.

Different composition pulp and textile fibers can be fed simultaneously to the respective lickerins in a side-by-side relationship. In one such embodiment, pulp and textile fibers are fed into the device toward the input end of the condensing zone to form a bottom layer of the web, while other materials are fed toward the exit end to form a top layer. In this way, different regions of the mixing zone can be defined corresponding to the input fiber materials, and the resulting web can be formed as horizontal and vertical layers or web zones. Each web zone is integrally associated with its adjacent web zone or zones by entanglement of the fibers across the interface; and each zone has a different but uniform composition of randomly oriented fibers.

When different fiber materials are introduced to each lickerin over different portions of each lickerin length, a layering effect is created. The bottom layer is formed first on the condensing means. It is created from the fiber material fed to the most rearward portions of the lickerin, which are deposited at a location on the moving screen beginning when it first enters the input or rear of the condensing zone. Successive layers may be formed by introducing different blends of fiber materials to the lickerins downstream of the rear end, with the top layer being formed by the blend of fiber materials fed to the most forward end of the lickerins.

This horizontal layering effect is distinct from the vertical fiber zones within each such horizontal layer. The vertical zones result from the transverse and diagonal deposition pattern caused by the doffing of fibers from the lickerins and their path of travel through the mixing zone and on to the condensing screen, a path which may be influenced by a vertical baffle and/or inclined shields in optional operating contact with the mixing zone and condensing zone, respectively. Moreover, the horizontal layers and vertical zones are independently formed, with the resulting composite web structure being defined by the number, types, and positions of the fiber materials fed to the lickerins, and the positions of the vertical baffle and/or inclined shields.

When a common vertical baffle is used, the transverse or lateral deposition patterns and resulting vertical zones within each layer of the web structure occur in groups, based on the groups of materials fed to each lickerin. However, a much wider variety of structures can be provided by incorporating a segmented baffle assembly into the apparatus. The segmented baffle comprises at least two baffle segments which can be selectively interposed within at least a part of the mixing zone and which can slide vertically with respect to each other. The segmented baffle defines sub-zones within the mixing zone, and these sub-zones correspond to portions of the operating length of the lickerins. In this manner, both the horizontal and vertical deposition patterns and the resulting horizontal layers and vertical zones can be varied in concert over each segment of the forming web, resulting in an extremely wide variety of heretofore unknown composite structures.

The invention also provides a segmented feed, which advantageously and selectively delivers different fiber materials to a lickerin along a portion or segment of the lickerin length. The segmented feed is adapted to adjust to the type of fiber and the desired end product, so that each different fiber material is fed to its portion of a lickerin under optimum conditions of speed, position and rate of delivery to the lickerin, etc. In particular, the segmented feed is adapted to selectively receive fiber materials of different types and thicknesses for fiberization at the fiberizing station, and the speed of the feed roller determines the concentration of those fibers in the web.

In yet another embodiment, the invention provides a method and apparatus for forming radially layered cylindrical nonwoven web structures. The cross-section of a web formed by a transverse webber need not be rectangular and layered. For some applications, e.g. tampons, a circular cross-section is desirable. This can be achieved by forming the web with a transverse webber on a U-shaped condensing screen. The U-shaped screen is then further bent into a circular form by guides. The deposition of fibers on the screen is made uniform by controlling the vacuum force through the screen such that it is a minimum at the center and increases towards both sides.

BRIEF DESCRIPTION OF THE DRAWINGS

The foregoing advantages and numerous other features of the invention will be more readily understood and appreciated in light of the following detailed description and accompanying drawings, wherein:

FIG. 3 is a side view of the apparatus of FIG. 2;

FIG. 4 is a fragmentary sectional view showing a portion of the condenser seals;

FIGS. 5–7 illustrate cross sections of exemplary composite nonwoven web structures;

DESCRIPTION OF ILLUSTRATIVE EMBODIMENTS

Figure 1:
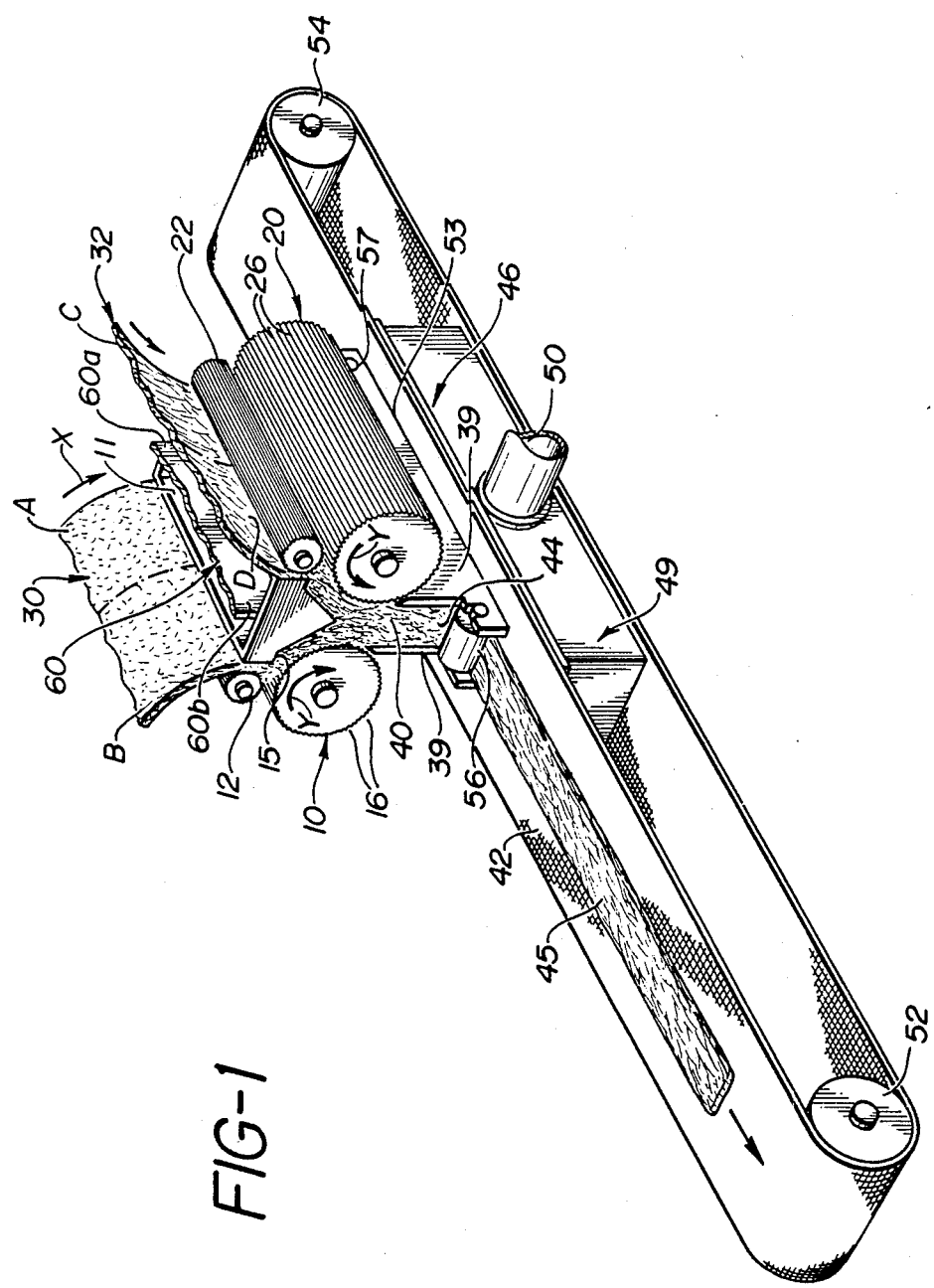
FIG. 1 is a schematic perspective view of a transverse webber according to the invention, showing the main components thereof.
Figure 2:
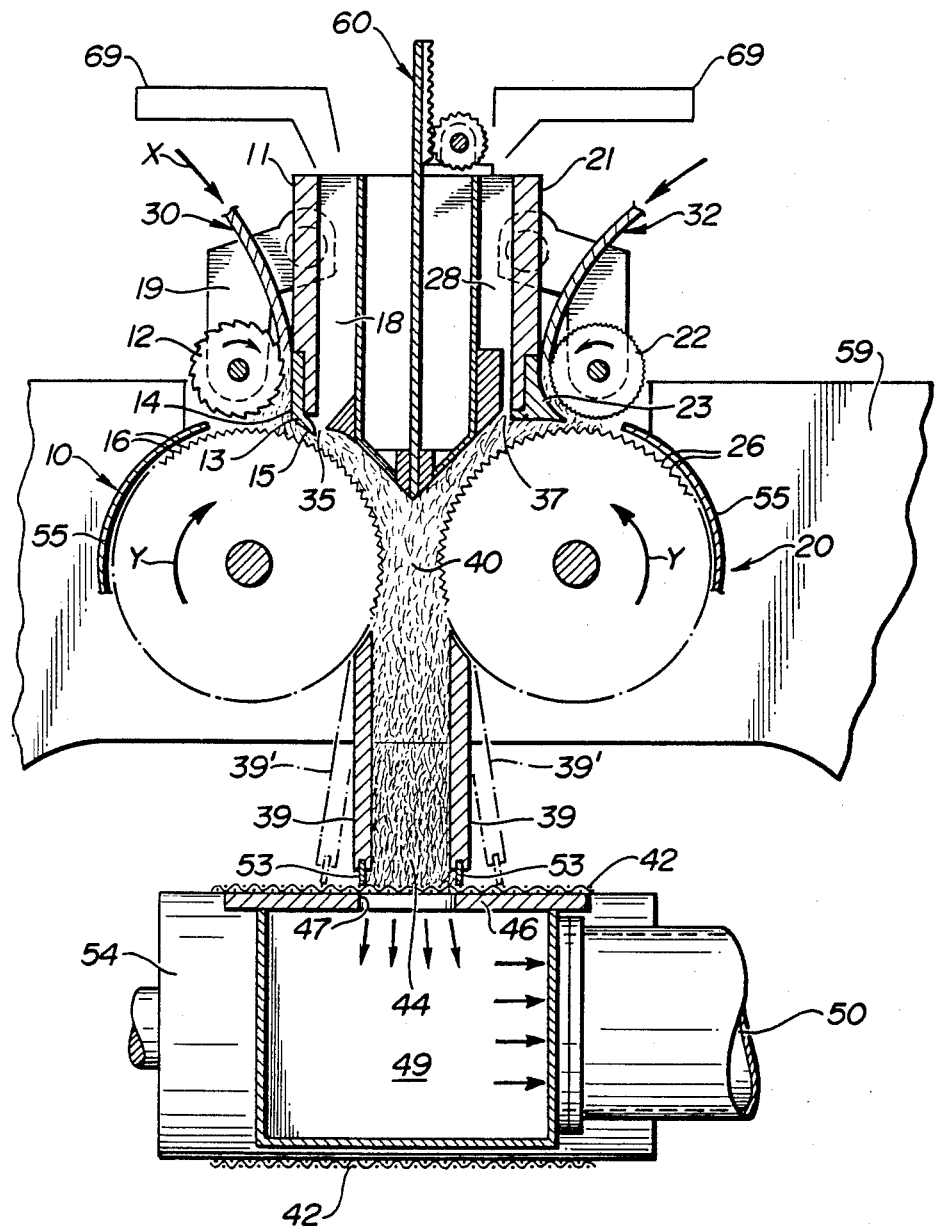
FIG. 2 is a more detailed cross-sectional view of an apparatus according to the invention.

FIGS. 1 and 2 show perspective schematic and cross-sectional views of the main components of an apparatus according to the invention. The invention is adapted to combine short and long fibers into a nonwoven web having variable horizontal and vertical cross-sectional compositions. Principally the apparatus comprises two lickerins 10, 20 operating in parallel. One lickerin 10 is adapted to individualize short fibers and the other lickerin 20 individualizes long fibers. The individualization of the fibers, but not the formation of the web, is generally performed according to commonly owned U.S. Pat. No. 3,740,797 to Farrington, the details of which are incorporated herein by reference.

Referring first to the short fibers, shown on the left in FIG. 1, wood pulp, in the form of a pulpboard 30, is directed between a plate 11 (FIG. 2) and a wire wound feed roll 12. The plate 11 has a nose bar 13 on its lower part, which provides an anvil for the pulpboard 30 during individualization of the short fibers. The fibers are individualized by the rotating lickerin 10 disposed below the feed roll 12 and operatively adjacent to the nose bar 13. The nose bar 13 assists in directing the pulpboard 30 along a path defined by the plate 11, the feed roll 12, the lickerin 10, the nose bar 13 itself, and an inclined face 15 adjacent to the lickerin 10. These elements form a fiberizing station where the fibrous material, i.e., pulpboard 30, is converted into individual fibers. The inclined face 15 is spaced a short distance from the teeth 16 of the lickerin 10 and the pulpboard 30 is individualized into fibers by the teeth 16 of lickerin 10 acting on pulpboard 30 as it is brought in contact with the teeth 16 by the nose bar 13.

Typical short fibers include wood pulp fibers from various types of wood, cotton linters, asbestos fibers, glass fibers, and the like. Wood pulp fibers are the most frequently used, due to their low cost and ready availability. Pulp fibers are commercially available in the form of pulp boards of varying sizes and thicknesses.

For short fibers, the nose bar 13 may have a relatively flat sidewall 14 (FIG. 2). The feed roll 12 is eccentrically mounted to permit adjustment relative to sidewall 14 and nose bar 13 as shown for example in FIG. 2 by bracket 19. The bracket 19 and feed roll 12 are resiliently biased to direct the pulpboard 30 against the nose bar 13 by known means, and to drive the pulpboard into proper engagement with the teeth 16 of lickerin 10. This design permits the use of pulpboards of varying thicknesses.

Feed roll 12 is supported on a shaft and is rotated by conventional motor means (not shown) at a speed determined by the rate at which the pulpboard 30 is to be fed to the lickerin 10. This rate determines the amount of pulp fibers deposited to form the web in a unit of time. The pulpboard 30 is fed to the feed roll 12 in the direction shown by the arrow X in FIG. 1.

The lickerin 10 is likewise supported on a shaft and is rotated at a predetermined speed by a conventional motor (not shown). Lickerin 10 is adapted to rapidly and reliably fray and comb the pulpboard 30 by engagement with the teeth 16 until individual fibers are liberated from the pulpboard. Speeds in the neighborhood of 6000 rpm have been found suitable for this purpose. The teeth 16 are chosen to have an optimum profile for the chosen short fiber material represented by pulpboard 30.

Long fibers are individualized in much the same manner as the short fibers, as shown on the right side of FIGS. 1 and 2. Typical long fibers include synthetic fibers, such as cellulose acetate, vinyl chloride-vinyl acetate and viscose staple rayon fibers, and natural fibers, such as cotton, wool or silk. Long fibers, such as rayon, are commercially available in bales, with varying fiber lengths.

A source of long fibers is provided, usually in the form of a carded batt 32, as when rayon is used as the fiber source. Batt 32 is introduced to lickerin 20 via a second wire wound feed roll 22 acting in cooperation with a plate 21 (FIG. 2) and a nose bar 23. However, the nose bar 23, adapted for use with long fiber sources, differs from the nose bar 13 used with pulp. Since rayon and other long fiber sources lack the physical integrity of pulpboard, the batt 32 must be more positively restrained and directed into engagement with the lickerin 20. As shown in FIG. 2, the nose bar 23 is curved to essentially conform to the adjacent surface of the second feed roll 22. In this manner, the fibers in the rayon source are maintained in position with respect to the second feed roll 22 until they are delivered to the teeth 26 of lickerin 20. The lickerin 20 is rotated at speeds such that the teeth 26 can comb long fibers from the batt 32 without degrading or damaging the long fibers. Speeds in the neighborhood of 3000 rpm have been found suitable for this purpose.

The teeth 26 of lickerin 20 are generally shorter than the teeth 16 of lickerin 10, and have a smaller pitch. Excellent results can be obtained when the tooth pitch and height of teeth 26 each range between about $\frac{1}{8}-\frac{1}{4}$ inches. The angle of teeth 26 varies between $-10$ and $+20$ degrees.

A support structure or frame and drive means are of course, provided for the various elements of the invention, as shown generally in the figures. Additionally, the nose bars, feed rolls, etc. can be adjusted with respect to each other in order to achieve optimal results.

The long and short fibers may be individualized simultaneously or sequentially, and as shown in FIG. 1 there may be more than one type of each fiber (i.e., short fiber pulpboards A, B and long fiber batts C, D) distributed over portions of each lickerin. The lickerins 10, 20 are rotated toward each other, as shown by the arrows Y in FIGS. 1 and 2. The fiber sources, their distribution, and the speed and relative proportions at which they are individualized, are chosen in order to produce a nonwoven web having the desired structure and combination of fibers.

The individualized long and short fibers are doffed from the lickerins, and are directed toward each other in a mixing zone 40. From the mixing zone the fibers pass to a condensing zone 44 containing a condenser screen 42. This movement of the fibers is assisted by air streams. As shown in FIG. 2, high velocity air streams, which doff the fibers and direct them to condenser screen 42, can be established by a suction force created by a high vacuum chamber 49 located below the screen. This vacuum is formed by a fan driven by a motor (not shown) and drawn through duct 50 (FIG. 2). The vacuum draws air through ducts 35, 37, past the lickerins 10, 20 and the nose bars 13, 23, through the mixing zone 40 and the condensing screen 42, to the chamber 49. Since the fibers travel the same path as the air streams from the lickerins to the mixing zone, the fibers are impelled to move more rapidly and reliably from the lickerins 10, 20 to the condensing screen 42, where they form the web 45. In order to assist in doffing fibers from the lickerins 10, 20, the air streams are directed at the lickerin teeth 16, 26 at a predetermined angle and velocity, causing a uniform flow pattern at and around the teeth. Advantageous manipulation of the air streams is further described in Farrington, U.S. Pat. No. 3,740,797.

The web 45 is formed in the condensing zone 44, which is a space below and proximate to the mixing zone 40, just above the condensing screen 42, and between duct plates 39. The length of the condensing zone 44 corresponds to the length of the lickerins 10, 20. Thus, the condensing zone 44, according to the invention, is in the form of a long trough adapted to receive individualized fibers from above.

The duct walls 39 shown in FIG. 2 are parallel and define the width of the condensing zone 44. However, these walls may be replaced with walls 39, that diverge (as shown in dotted line) at angles up to 15 or 20 degrees, in order to form a web wider than the separation of the lickerins (FIG. 2).

The condensing screen 42 preferably comprises an endless conveyor that is guided over conveyor rollers 52, 54, (FIG. 1), such that it may pass about the high vacuum chamber 49. One or both of the rollers 52, 54 are driven so as to move screen 42 at a controlled rate.

When using entraining air streams, the vacuum chamber 49 will communicate with the condensing zone 44 through the mesh screen 42 via a suitable aperture 47 provided in suction plate 46 (FIG. 2). The aperture generally corresponds to the cross section of the space defined by the duct plates 39 and 59. The conveyor screen 42 is positioned to travel below and in communication with the condensing zone 44, and in a direction that is parallel to the axes of rotation of the parallel lickerins 10, 20. As a result, the web 45 is formed as a continuous sliver expelled from the condensing zone 44 at right angles to the direction of the fiber supply input and transversely with respect to the rotating lickerins 10, 20. The web 45 is not condensed, as it is in known devices, in a plane formed beneath the lickerins, having a width corresponding to the length of the lickerins, and moving perpendicular to the axis of rotation of the lickerins.

The thickness of the web according to the present invention is inversely proportional to the speed of the screen 42. The faster the screen 42 withdraws the forming web 45, the thinner the resulting web. However, the structure and orientation of the present condensing zone 44 with respect to the mixing zone 40 permits much thicker, albeit narrower, webs to be formed far more rapidly than by other prior techniques.

The screen 42 may communicate with other conveyors, thereby delivering the web 45 for further processing as desired. Such processing may include bonding, as described for example in Lovgren, U.S. Pat. No. 3,772,739; shape-forming procedures; and final finishing of the web product.

In order to seal off the lower ends of ducts 39 and to maximize the efficiency of the suction fan, duct plates 39 are extended downward toward the screen 42 and terminate just above the screen 42. The duct plates 39 may additionally be provided with floating seals 53, which are biased into contact with the screen 42 by a spring located behind the floating seals in a recess in plates 39 (FIG. 4.. Lickerin covers 55 (FIGS. 2 and 8B) may also extend about the outer periphery of the lickerins and engage plates 39 to provide an additional seal for the vacuum which forms the air streams.

At the places where the screen 42 enters and leaves the condensing zone 44, rolling seals 57, 56, respectively, are provided on duct plates 59 (FIG. 3). The sealing rolls 56, 57 are disposed between the parallel edges of duct plates 39 and are free to rotate on the screen and web to accommodate movement of the screen and web. When the web 45 exits the condensing zone 44 supported by the screen 42, it passes beneath sealing roll 56. Besides maintaining the vacuum, the duct plates 39 serve to guide the fibers to the condensing zone 44 and together with the plates 59, the floating seals 53, and sealing rolls 56, 57, they improve the efficiency of the suction air flow.

Figure 7:
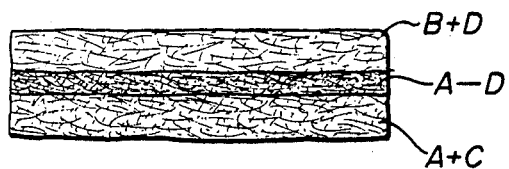

The device of FIGS. 1 and 2 is provided with a retractable baffle 60 disposed within a plane passing perpendicularly between the lickerins 10, 20 and intersecting the mixing zone 40. Although the baffle can be placed so that its downward leading edge falls at any predetermined point at or above the moving condenser screen 42, three distinct qualitative positions can be defined. When the baffle 60 is in the up or fully retracted position, its leading edge is removed from any functional contact with the fiber streams leaving the lickerins. When the baffle 60 is fully down, its downward leading edge is at or above the screen 42 at a predetermined position within the mixing zone 40 where it completely intercepts the fiber streams. Finally, the baffle 60 can be positioned so that its downward leading edge corresponds to a predetermined blend point within the mixing zone 40 where it partially blocks the fiber streams. A wide variety of composite structures can be generated by varying the position of the baffle 60 and by feeding one or more materials via each of the feed rolls 12, 22. FIGS. 5-7 illustrate exemplary composite nonwoven web structures as described according to the following examples. It will be understood by skilled practitioners that these examples represent only a few of the many structures that can be made. Moreover, it will be evident from the examples that, because of the transverse discharge of the web 45, a uniformly blended web is formed which is unobtainable in the same manner in known devices, such as the Farrington method and apparatus. On the contrary, the transverse webber tends to deposit the fibers into a web according to unique zone-forming patterns. These patterns can be manipulated to produce new and useful composite structures.

EXAMPLE 1

The same fiberizing stations (i.e. lickerin, nose bar and feed roller) are set up at each side of the screen. Then identical short fiber pulpboards 30 or long fiber batts 32 are supplied to both of the lickerins 10, 20, via the feed rolls 12, 22. The resulting web 45 is a homogeneous nonwoven web consisting of one kind of fiber. The result is the same for any position of the baffle 60.

EXAMPLE 2

Two different fiber materials 30, 32 in the form of short and long fibers A, C, respectively, are delivered to the feed rolls 12, 22 respectively, with each different fiber source being coextensive with one of the lickerins 10, 20. When the baffle 60 is in the up position, a composite web is formed having three lateral zones, each running in the machine direction. A schematic cross-sectional view of this product is shown in FIG. 5.

The zone-like composite structure is a consequence of the trajectories of the fibers doffed from the lickerins, passed through the mixing zone 40 and then formed into a transverse web within the condensing zone 44. In a conventional webber, any such nascent zones tend to be cancelled or unified by continuous withdrawal of the forming web in the standard longitudinal machine direction, i.e. the direction in which such zones would form. However, by withdrawing the forming web in the transverse direction, the zones form as a result of the fiber deposition pattern caused by the fiber trajectories.

When the baffle 60 is up, it does not alter the dilute fiber/air stream trajectories as they pass through the mixing zone 40 to the condensing zone 44. The fibers within the air streams retain a component of motion tending to throw them away from their respective lickerin and toward the web on the side of the opposing lickerin. As a result, the fibers tend to pass each other within the mixing zone 40 because the streams are so dilute that there is little tendency for fiber collisions. Thus, the fibers are predominantly deposited toward opposite sides of the condensing zone 44. As shown in FIG. 5, short fibers A originating from a left-hand lickerin tend to form a narrow right-hand fiber zone A containing predominantly fibers A. The long fibers C originating from the right-hand lickerin tend to form a narrow left-hand zone C containing predominantly fibers C. Between the fiber zones A and C is a wider transition zone containing a blend of fibers A+C. At the boundaries of the zones the fibers are entangled so that the web is formed in one piece.

EXAMPLE 3

The fiber sources of Example 2 are used, but the baffle 60 is positioned at a blend point within the mixing zone 40 in order to influence the trajectories of the individualized fibers prior to final deposition as a web on the screen 42. The individualized fibers passing through the mixing zone 40 and on to the condensing zone 44 from each lickerin fall within a range or angle of trajectories, in the manner of a spray exiting a nozzle. The baffle 60, when positioned at the predetermined blend point, intersects at least part of the trajectory angle, causing some of the fibers and any entraining air flow within that part of the angle to bounce off the baffle 60 back toward its own originating side of the condensing zone 44.

If the baffle blend point is chosen so that approximately equal volumes of fiber from each lickerin are redirected by the baffle 60, as are permitted to pass under the baffle 60 without interruption, a uniformly blended web of short and long fibers A+C is obtained. The blend point can, of course, be chosen to provide a wide variety of fiber deposition patterns and resulting nonwoven web structures.

EXAMPLE 4

In yet another embodiment, the baffle 60 is placed in a down position, approximately 2 inches above the screen 42. The two different fiber sources A, C of Example 2 are used such that each fiber is supplied over an operative length of one of the parallel lickerins 10, 20. In this case, substantially all of the fiber trajectories are interrupted by the baffle, tending to throw the fibers back toward their originating side of the condensing zone 44. The result is a web similar to the web in Example 2, but with the fiber zones A and C in reverse order, and a narrower transition zone A+C as shown in FIG. 6.

It should be appreciated that regardless of the position of the baffle, there will be some distribution of both long and short fibers across the web due to the turbulent air flow. Thus the zone representations in FIGS. 5 and 6 merely show the predominant fibers in each. The proportion of fibers in each zone may also be regulated by the rate at which the fiber sources 30, 32 are fed to the lickerins. A fiber fed at a faster rate will produce a greater concentration of that product in the web, although it will be distributed across the web in a manner determined by the baffle position.

Each lickerin 10, 20 need not be supplied entirely with one fiber source, provided that all of the fibers supplied to each lickerin conform to the fiber type (short or long) for which the lickerin is adapted. Thus, for example, four fiber sources A-D can be equally distributed among the two lickerins, each such source covering half of its respective lickerin. FIG. 1 illustrates this embodiment. The pulpboard 30 has a portion with short fibers A and another portion with short fibers B, both of which are fed to lickerin 10. Textile fiber batt 32 also has two portions for producing long fibers C, D which are fed to lickerin 20. The fiber combination A, C toward the input end of the apparatus produces a lower layer of the web, while the fiber combination B, D toward the exit end of the apparatus produces an upper layer. Thus, the resulting product has both lateral zones, and vertically-arranged zones or layers of fiber compositions.

EXAMPLE 5

The multiple fiber supplies A-D of FIG. 1 are fed to the apparatus with the baffle in a blend point position to promote uniform mixing and deposition of fibers. The two rearward fiber sources A and C in the machine direction apply their fibers on a portion of screen 42 first. As this portion of the screen moves toward the exit it passes below the transition between sources AC and BD, and a transition layer having a mixture of all four fibers is laid down on top of the lower layer, which is a uniform blend of fibers A and C. As the screen portion moves under the region of the lickerins which is fed fibers B, D, these are deposited as an upper uniformly blended layer B and D. A cross section of this product is shown in FIG. 7.

EXAMPLE 6

Figure 8A:
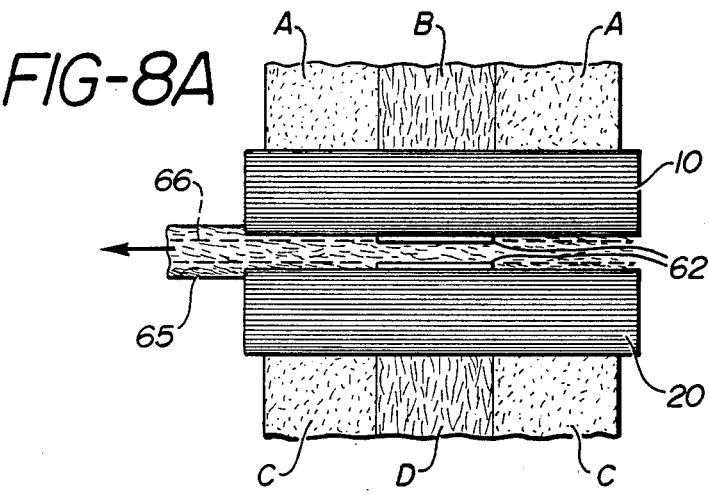
FIGS. 8A and 8B are schematic top and end views of an apparatus according to the present invention with a fixed shield installed in the condensing zone.
Figure 8B:
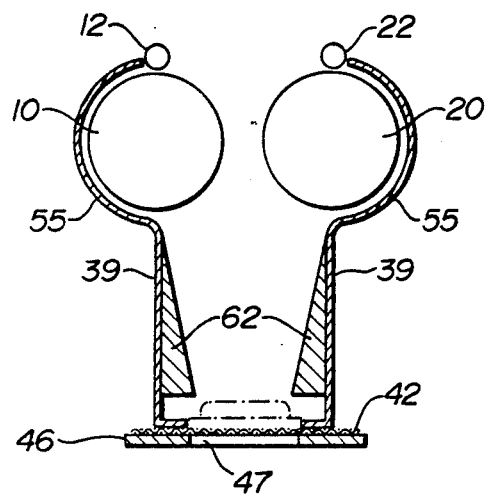
Figure 9A:
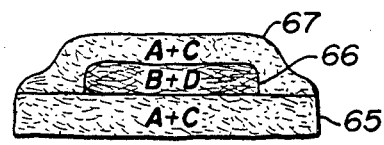
FIGS. 9A and 9B are cross-sectional and top views, respectively, of a product made according to the apparatus of FIG. 8.

An alternative product as shown in FIG. 9 may be made by installing fixed shields 62 (FIG. 8A and 8B) in the condensing zone 44 toward the middle of the machine and feeding three separate portions to the lickerin, i.e. A and C, B and D and A and C. The fixed shields 62 are generally disposed at a horizontal position above the forming web in the middle where fiber portions B and D are laid down. Thus a first wide layer 65 is deposited which is a mixture of fibers A and C. (FIG. 9A). Then a middle layer 66 can be added. This layer is narrower and comprises fibers B and D because shields 62 make the condensing zone narrower (FIG. 8B). Finally, a third or top layer 67 is added. Layer 67 may also be a blend of fibers A and C so that the middle layer 66 of fibers B, D is completely surrounded by fibers A and C.

A product in which a middle layer is surrounded by other layers can be very advantageous as an absorber, e.g. a diaper or sanitary napkin. With such a product the inner fiber blends, e.g. B and D, in layer 66 of FIG. 9A, are selected to be high absorbency fibers. For example this layer may be made predominately of pulp or superabsorbing fibers. The outer fibers, e.g. A and C are selected for their wicking properties, i.e. the ability to move liquid. For example, Rayon fibers have good wicking properties. With such a product the moisture is directed away from the user's skin and clothing by the wicking fibers and is retained in the center of the product by the high absorbency fibers.

Figure 9B:
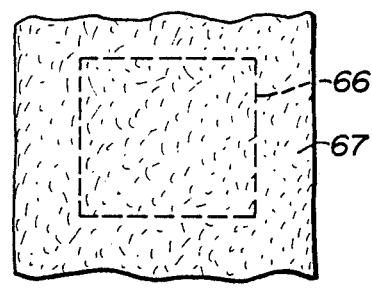

If the feeding of the pulp or high absorbency fibers is intermittent, separate patches of this material will be buried along the web (FIG. 9B). In later processing the web can be separated between these patches to form individual products. For example, these products may be surgical pads with absorbent, inexpensive, but unattractive pulp layers, concealed by a polyester cover layer.

EXAMPLE 7

As a further modification, powder dispensers in the form of trays 69 may be located above plates 11, 21 as shown in FIG. 2. These dispensers may be used to introduce super absorbent powders or other materials into the web as it forms by introducing the materials into the air streams that doff fibers from the lickerins. In particular, the doffing air streams are created by a suction force in chamber 49. This draws air from the atmosphere, through channels 18, 28, over the lickerins, through mixing zone 40, through condensing zone 44 to chamber 49. By placing trays 69 at the entrance to channels 18, 28, the particulate material in the trays is drawn into these channels and mixes with the fibers formed at the lickerins.

If these trays are positioned near the center of the axes of the lickerins, the particulate material will end up in the center of the web. In particular, a first layer, e.g. one predominated by fibers with good wicking properties can be laid down by feeding fibrous material of this type in the positions A and C in FIG. 1. Then, as the forming web moves under the part of the lickerins where the trays 69 are located, the fibers will be mixed with, e.g. super absorbent powder. Also, the fibers in this zone may be predominantly absorbent, e.g. pulp. Thus a highly absorbent middle layer is formed. This layer may be made narrower than the bottom layer if shields 62 (FIG. 8B) are included in the region below the tray 69. Finally a top layer of good wicking fibers is added to the web just before it exits the condensing zone. In this way, the invention provides a super absorbent core surrounded by fibers that provide good wicking properties.

EXAMPLE 8

Figure 10:
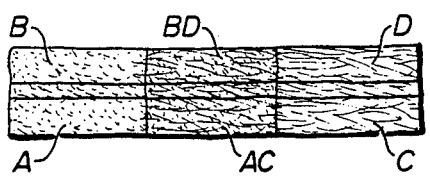
FIGS. 10-15 illustrate cross-sectional views of products according to the invention having horizontal and vertical web zones.
Figure 11:
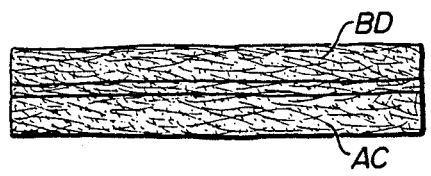
Figure 12:
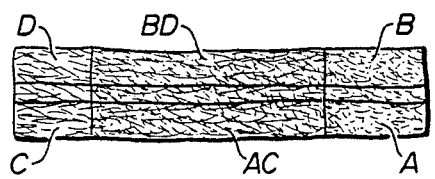

FIGS. 10-12 show a horizontal layering effect achieved by the invention when different fiber materials are fed to the lickerins along segmented portions of the lickerin length, in cooperation with a common vertical baffle 60 (FIG. 2). The blend of fibers doffed and condensed at the rear form the bottom layer. Successive layers corresponding to each different lickerin segment are deposited over the bottom layer as the forming web moves downstream, from the rear to the front.

When a common baffle 60 is used, it controls the blending of fibers in vertical zones without regard to the number of parallel supplies of fiber material. In the example of FIGS. 10-12, which is representative of this phenomenon, four different fiber materials are supplied, each being coextensive with half the operating length of a lickerin. Thus, fibers A and B are fed to one lickerin and fibers C and D are fed to the other, with A and C being fed at the rear and B and D being fed at the front, as in Example 5. Fibers A and C will be deposited first, to form a bottom layer, followed by overlapping deposition of fibers B and D to form a top layer. As shown by FIGS. 10, fibers A and C will always be grouped together horizontally and fibers A and B will always be grouped together vertically. Similarly, fibers B and D will always be together horizontally and C and D will always be together vertically. The position of the common vertical baffle 60 does not change this relationship, although it does change the blend composition and horizontal positions of the fibers in the product.

FIG. 10 shows a product according to an embodiment where the baffle 60 is fully down, resulting in a composite material having three horizontal layers (B, BD, and D on top; A, AC, and C on the bottom), and a thin horizontal transition layer between the other two horizontal layers.

FIG. 11, which is similar to FIG. 7, shows a product according to an embodiment where the baffle 60 is positioned at a blend point within the mixing zone. The result is a three layer composition: a bottom layer of A and C uniformly mixed according to predetermined proportions, a top layer of B and D uniformly mixed according to predetermined proportions, and a thin transition layer between them.

FIG. 12 shows a product according to an embodiment where the baffle 60 is fully up, resulting in a composite product formed generally as a mirror image of the product shown in FIG. 10, except that the central blended vertical zones of fibers BD and AC are wider.

Figure 16:
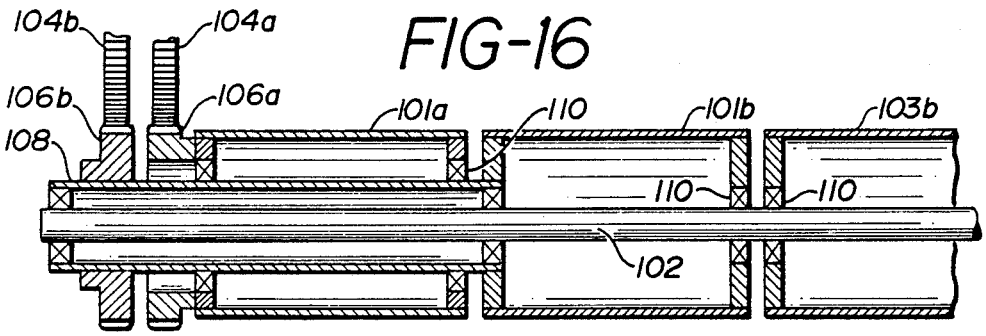
FIG. 16 shows a sectional view of a segmented feed roller according to the invention.

Instead of one piece, baffle 60 may be formed as segmented baffle 60a, 60b with two or more sections (FIG. 1). Each segment of the baffle corresponds to a different portion of the operating length of the lickerins. In a preferred embodiment, each segmented baffle corresponds to a different pair of input fiber materials, optionally delivered by segmented feed rollers, as shown in FIG. 16.

EXAMPLE 9

Figure 13:
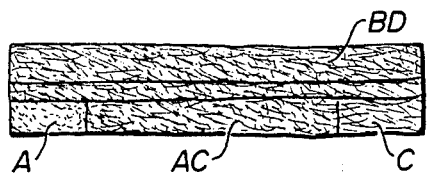
Figure 14:
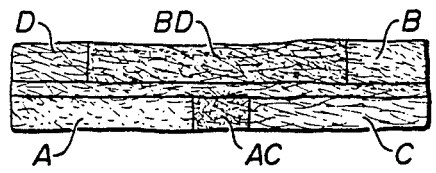
Figure 15:
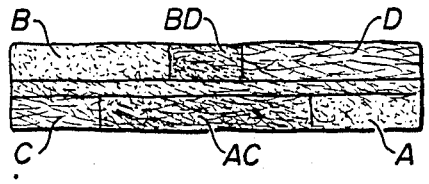

FIGS. 13-15 represent products obtained with a segmented baffle, where fiber materials A and C are fed to a rear segment of their respective lickerins within a lickerin length corresponding to a first baffle segment 60a vertically and optionally disposed within at least part of the mixing zone (FIG. 1). Fiber materials B and D are fed to a front segment of their respective lickerins within a lickerin length corresponding to a second baffle segment 60b. The baffle segments can be positioned independently in the up, down or blend positions, to achieve a very wide variety of composite shapes.

FIG. 13 shows a product obtained when the first baffle segment 60a (corresponding to fiber materials A and C) is down and second baffle segment 60b (corresponding to fiber materials B and D) is in a blend position. This arrangement results in a bottom layer of materials A, AC and C deposited due to interference with the fiber streams from the baffle, a blended top layer of fiber materials B and D, and a thin transitional layer between the top and bottom layers. Essentially, the segmented baffle results in this instance in a composite structure combining the bottom layer of FIG. 10 with the top layer of FIG. 11.

In FIG. 14, the product is created by the device with the positions of the baffle segments 60a and 60b altered with respect to their positions for the creation of the product of FIG. 13. When the first baffle segment 60a is down and the second baffle segment 60b is fully up, a multi-layer and multi-zone structure is formed, combining the top layer of FIG. 12 with the bottom layer of FIG. 10. These positions are reversed to form the product in FIG. 15, with first baffle segment 60a fully up, and second baffle segment 60b fully down.

It will be appreciated that an extremely wide variety of new composite structures can be generated by the manipulation of baffle segments corresponding to different fiber materials input over different portions of a lickerin length, the different fiber materials being chosen and positioned to produce a horizontally layered nonwoven web having vertical zones.

The invention also provides for segmented feed rollers, as shown in FIG. 16. The segmented feed provides a means of advantageously delivering different fiber materials to different segments or longitudinal portions of each lickerin at varying rates. In this manner, different fiber materials of the same type (e.g. long or short), can be readily fed to a single lickerin, and corresponding pairs of materials can be fed to parallel portions or segments of the parallel lickerins in a transverse webber, in order to provide composite nonwoven web structures having different blend ratios for any pair of materials being fed to the lickerins.

The segmented feed assembly comprises at least two feed roll segments 101a, 101b (FIG. 16) mounted on a common stationary shaft 102. The feed roll segments are each selectively adapted to receive particular fiber materials for delivery to a common lickerin at different predetermined rates, over a longitudinal portion or segment of the operating length of the lickerin. In this way, the blend ratio can be altered and optimized, depending on the desired end products, and more than one blend ratio is possible.

The blend ratio of a composite web is a function of the weight per unit area of the incoming individual fibers as determined by the rotational speed of the feed roll. With a conventional feed, there are only two feed rolls, one for each lickerin, each operating at a compromise speed chosen according to the fibers to be individualized and the desired end product. Thus, the use of a conventional feed in a transverse webber can result in only one blend ratio of left-hand fibers to right-hand fibers, no matter how many different fiber compositions are introduced along the operating length of each lickerin. The segmented feed permits a plurality of blend ratios, each confined to its own lickerin segment.

Motors (not shown) are used to drive gear trains that mesh with gear 104a, 104b. Gear 104a meshes with a gear 106a that is rigidly fastened to an outer end of feed roll segment 101a. As a result, feed roll segment 101a will rotate and feed material to its corresponding lickerin portion at a rate determined by the rotation of gear 104a and the gear ratio of gears 104a and 106a. Likewise, gear 104b meshes with a gear 106b that is rigidly attached to feed roll segment 101b by a cylindrical drive shaft 108. Shaft 108 is also mounted on the common stationary shaft 102. As a result, feed roll segment 101b is rotated and feeds material to its lickerin portion at a rate determined by gear 104b (which rate is independent of the speed of gear 104a) and the gear ratio of gears 104b and 106b.

By means of bearings 110, the cylindrical shaft 108 and the feed roll segments 101a and 101b are rotatable with respect to stationary shaft 102.

Should more than two feed roll segments be desired for a single lickerin, e.g. four segments, the other feed roll segments, e.g. 103b, may be driven in the same way as that shown in FIG. 16 for segments 101a, 101b, except reversed so that the drive mechanism, i.e. the gears, are located toward the outer edges of the feed roll assembles, as opposed to having part in the middle, which would cause a break in the fiber flow streams. Feed roll segments could be driven by other mechanical means than the gears shown, e.g. by chains or belts.

EXAMPLE 10

Figure 17A:
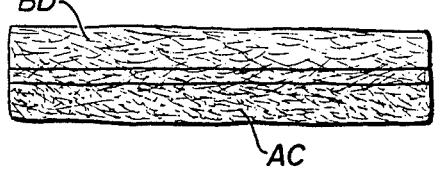
FIGS. 17A and 17B show a composite product made with a segmented feed apparatus according to the invention.

FIG. 17 illustrates a product made using the segmented feed, compared with one made using a conventional feed. Fiber materials A and B are processed on one lickerin and C and D are processed on the other lickerin, with A and C at the rear and B and D at the front. All of the fiber materials are of equal length along the lickerins. If a common baffle 60 is at a blend position, a composite material results, comprising a blend of A and C as a lower layer and a blend of B and D as an upper layer, with a fixed blend weight ratio of A/C=B/D (FIG. 17A).

Figure 17B:
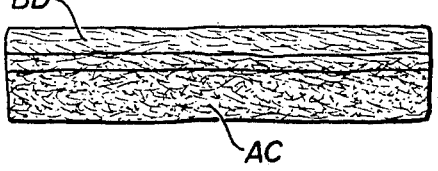

But, if the feed rolls are segmented as shown in FIG. 16, using the same fiber materials and distribution A–D, such that each lickerin is provided with two different fiber materials at two different speeds, then the blend ratios become variable. One such embodiment, where the ratios A/C and B/D are independent, is shown in FIG. 17B. Here the feed rollers for fibers A, C are rotated at a higher speed than the segments for fibers B, D. Consequentially, the lower region of the web is thicker than the upper layer.

As an alternative, the A fiber segment may be rotated at a higher speed than the B segment, so that in the lower layer there is more A fiber than there is B fiber in the upper layer. Thus, in FIG. 17A wherein the segments of each feed roll have the same respective speed, the fiber ratios are the same for each layer, i.e., A/C=B/D. However, in FIG. 17B a product is shown where the B segment is rotated slower than the A segment so that A/C>B/D. Other variations are obvious from the ability to simultaneously feed materials to different lickerins or different parts of the same lickerins at different independent rates.

Figure 18:
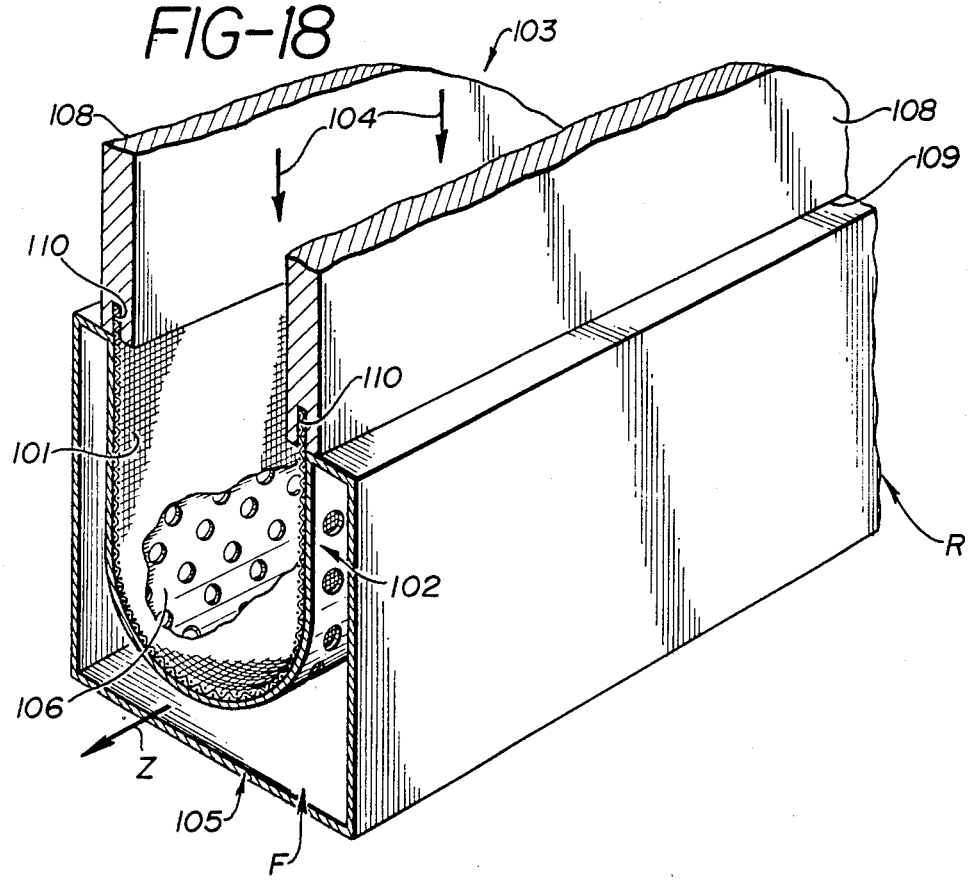
FIG. 18 shows a perspective view, partially in section, of an apparatus for forming radially layered and cylindrical nonwoven fibrous structures.
Figure 19:
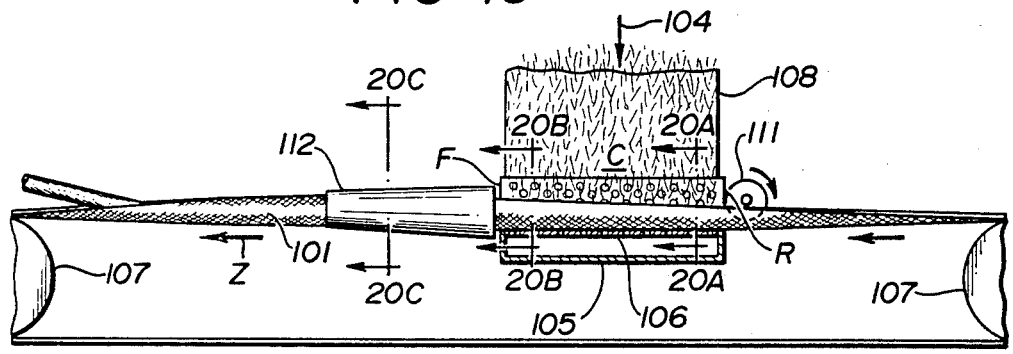
FIG. 19 shows a side elevation of an apparatus for forming radially layered and cylindrical nonwoven fibrous structures.
Figure 20A:
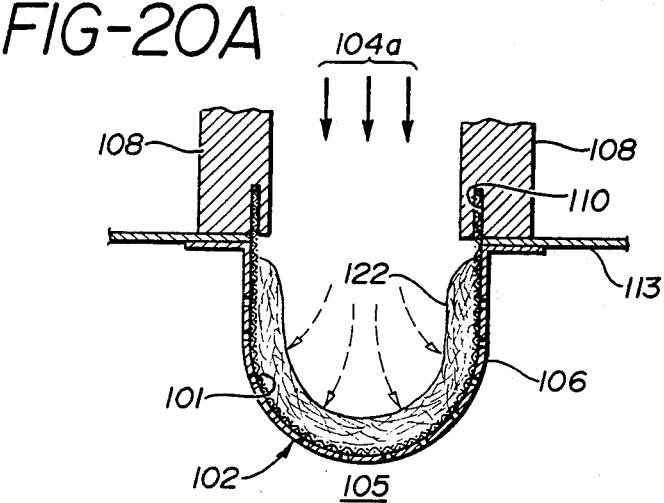
FIGS. 20A-20C schematically illustrate a method of forming cylindrical nonwoven structures according to the invention.

Still another embodiment of the invention is shown in FIGS. 18–20, which illustrate an apparatus for forming radially layered cylindrical nonwoven structures on a transverse webber. In such an apparatus, the condensing means, as shown in FIGS. 18 and 19, comprises a flat, continuous and flexible screen belt 101 moving in a machine direction that is transverse to the plane within which the lickerins are rotating, i.e., parallel to the lickerin axes. The direction of travel of the belt 101 also defines a rear end R, where the belt 101 first enters the condensing zone C and first receives fibers. The front end F is the point where the belt 101 exits the condensing zone C and ceases to receive fibers.

The belt 101 is at least partially confined within a U-shaped trough 102 disposed beneath the mixing zone 103 of a fiber webber, from which the belt 101 receives fibers doffed from the lickerins and mixed in the mixing zone, as entrained by fiber-carrying air streams 104. The air streams 104 are created or supplemented by a vacuum chamber or suction box 105 disposed below the trough 102 and the belt 101, and communicating with the belt 101, preferably through a perforated support 106. The belt 101 is driven through the trough 102 and beneath the mixing zone 103 by rollers 107 and conventional motors (not shown), with the direction of motion indicated by the arrows Z in FIGS. 18 and 19. The mixing Zone 103, belt 101, trough 102, perforated support 106 and suction box 105 provide a downward vertical path for fibers and their entraining air streams 104. The fibers exit the mixing zone 103 under the influence of gravity and the streams 104 and are deposited on the belt 101, causing the forming web to conform to the U-shape imposed on belt 101 by trough 102. The air streams 104 continue through the condensing fibers, belt 101, and perforated support 106, and operationally terminate within suction box 105. In this manner, many new composite web structures having non-rectangular cross-sections may be produced.

In a preferred embodiment, the trough 102 and the corresponding U-shaped portion of belt 101 are coextensive with the mixing zone 103, which in turn is coextensive with the condensing zone C and the operating length of the lickerins of the transverse webber, which in turn corresponds to the front and rear ends, F and R.

As shown in FIGS. 18 and 19, parallel duct plates 108 descend from the mixing zone 103 to create seals 109 with the trough 102 (FIG. 18), in order to assist the suction created by suction box 105 and to confine the air streams and fibers within an optimum condensing zone. In the preferred embodiment, the duct plates 108 are provided with recesses 110, which are adapted to receive the edges of the belt 101 as it passes through trough 102 and is deformed into the desired U-shape. Thus, the condensing zone C is advantageously contained and preferably sealed within a volume defined by the mixing zone 103 above, the U-shaped portion of belt 101 below, the duct plates 108 at the sides, and the front and rear ends, F and R, Which may contain rolling seals.

The belt 101 is not U-shaped over its entire continuous length. Instead, the belt 101 arrives proximate to the rear end R as a flat continuous belt. Means, e.g., in the form of sealing roll 111, are provided to partially deform the belt, so that it may be received by the trough 102 and further deformed into the desired U-shape over the desired length. The forming roller 111 is biased into contact with the belt 101 and also serves to seal the rear end R of the condensing zone C, with respect to the fibers and air streams 104. A similar roller, not shown, may be located at the front end F, but is not necessary because of the sealing effect of the forming web tube and guide plates 112.

In the exemplary embodiment of FIGS. 18 and 19, the forming roller 111 partially deforms belt 101, so that its edges leave the flat plane within which the belt is traveling, whereupon the edges may be entrained within recesses 110 and drawn against support 106 by the suction force.

Figure 20B:
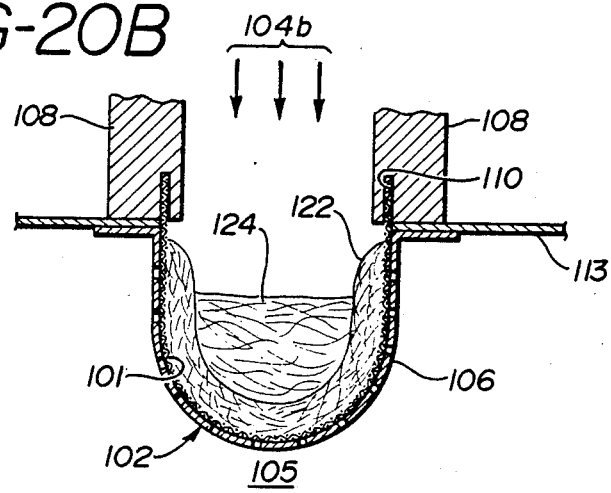
Figure 20C:
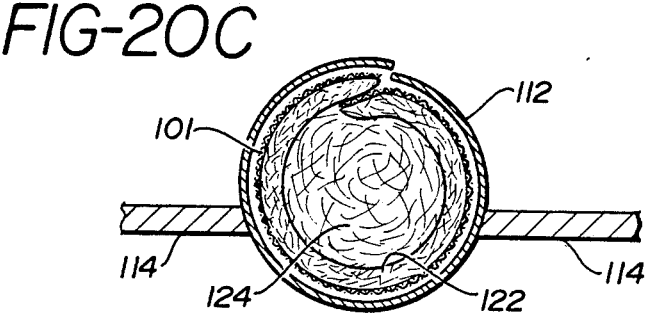

As the U-shaped portion of belt 101 exits the trough 102 at the front end F, the suction force is eliminated and it is delivered to forming shoes or guide plates 112, which may be in the form of a convergent-divergent forming tube as shown in FIGS. 19 and 20C. In this manner, the U-shaped belt portion 101 and the formed web it now carries are further deformed into a cylindrical shape, so that a composite web structure having radial layers and a circular cross section is formed. The now cylindrical product is moved further along, and the guide structure opens up and allows the product to exit the guide 112. The web product is then separated from the belt 101, and belt 101 is permitted to collapse back to its flat configuration. It then travels about rolls 107, and eventually back to the condenser zone.

In operation, a homogeneous cylinder can be obtained by feeding only one material to the lickerins, or by feeding two materials, one to each lickerin, to obtain a homogeneous blend. Radially layered structures can be obtained by feeding materials to the lickerins toward the rear end R which are different than the materials fed toward the front end F.

The operation of the apparatus and a method of making cylindrical composite structures, are illustrated by FIGS. 20 A-C, which are drawn along the section lines AA', BB', and CC' of FIG. 19, respectively.

A uniform layer of fibers 122 (FIG. 20A) can be achieved, despite gravity effects, by controlling the airflow distribution through the screen belt 101, for example by selectively perforating the support 106 and/or subdividing the suction box to provide independent suction to different cross-sectional areas of the belt 101 as it passes through the condensing zone C.

Since gravity and the trajectories of the fiber from the lickerins would tend to cause most of the fibers to accumulate at the bottom of trough 102, i.e. at the center of the web, action must be taken to make the height of the formed web uniform. To accomplish this, the airflow differential provided by suction box 105 must oppose the gravity and inertial fiber forces that tend to deposit all of the material at the bottom of the "U", while leaving the vertical sides uncovered. This may require that there be no suction force at the bottom of the U-shape and maximum force at the vertical edges.

The suction at the vertical sides must be maintained throughout the condensing zone so that the layer 122 toward the edges is held on the screen. However, as the web moves towards the front end F, suction is also provided at the bottom of the U shape in order to form a center core of material 124 about which the layer 122 may be wrapped by the screen to form a cylindrical product.

EXAMPLE 11

Fiber materials are individualized by lickerins, doffed, and the individualized fibers are entrained in air streams 104 promoted by a suction means in the suction box 105. In the embodiment shown, the trough 102, perforated support 106 and the U-shaped portion of belt 101 are disposed within a recess in the top of the suction box 105. The duct plates 108 form a mutual seal with the trough 102 and a suction box wall 113.

In a first phase of operation, shown in FIG. 20 (section 20A–20A of FIG. 19), a first mix of fibers e.g. those with good wicking properties are entrained in a first stream 104a toward the rear end R. These fibers are deposited on the U-shaped portion of belt 101. The suction is controlled so as to influence the air streams in a predetermined manner, resulting in a desired deposition pattern of a generally uniform height on the U-shaped belt. In this manner, the fibers are distributed in a uniform U-shaped outer layer 122, over a rearward portion of the condensing zone C corresponding to the fiber material introduced to a corresponding rearward portion of the lickerins.

In a second phase, the belt 101 moves forward, carrying layer 122. As shown in FIG. 20B, a second mix of fibers, e.g. high absorbency fibers, is entrained in a second stream 104b and is deposited on top of layer 122 as a core layer 124. Suction may again be advantageously controlled to influence the fiber deposition, but is less critical during this phase. In fact the suction may be predominantly in the middle so as to form the fibrous structure shown in FIG. 20B. The rate of fiber deposition is controlled, so that the resulting layer 124 achieves a desired depth. In the embodiment shown, the core layer 124 has a depth that is less than the depth of the trough 102, and the top of the layer 124 is below the walls of outer layer 122.

Once the core fibers are deposited as layer 124 within a forward region of condensing zone C (corresponding to section 20B—20B in FIG. 19), the U-shaped portion of belt 101 exits the condensing zone C at the front end F.

In a third phase, shown in FIG. 20C (section 20C—20C of FIG. 19), the belt 101, which now supports a condensed web having a curved cross section, is introduced to forming shoes or guides 112 supported by a shoe support 114. In the embodiment shown, the shoes 112 are in the form of a convergent tube. The belt 101 and the web containing layers 120 and 124 are further deformed by guides 112 into a circular shape. When the depth of core layer 124 is less than the depth or circumferential length of layer 122, as shown, the guides 112 cause the ends of outer layer 122 to meet, thereby uniformly enfolding the core layer 124 within a cylindrical outer layer. If outer layer 122 contains a heat fusible material, heat may be applied to the outer layer to stabilize circumferentially the structure to keep the product in the cylindrical shape.

The resulting nonwoven cylindrical product is a uniform radially layered web having an inner core of absorbent material surrounded by a sheath of material with good wicking properties. The composite web has a circular cross-section, and may be adapted to a number of uses. For example, an advantageous feminine hygiene tampon product can be obtained by providing a core layer of highly absorbent fibers and an outer layer of fibers having good wicking properties. In another embodiment, highly absorbent particles delivered to the air stream 104b can be substituted for some or all of the highly absorbent fibers.

It will be appreciated by skilled practitioners that many more radially layered products can be made according to this method and apparatus, and that the specific embodiment described is illustrative rather than limiting.

Other Variations

Various other products can be made in segments by starting and stopping the condenser screen and by starting and stopping or sequentially feeding the various fiber materials to the lickerins. Also, fibers may be included which provide properties to the product other than moisture handling. For example a fibrous material with great resiliency may be used to give a product, e.g. a napkin, a springy characteristic that makes it feel like a plush material.

As another example, the product shown in FIG. 7 can be formed with the present invention to have a top layer of 70% polyester and 30% synthetic pulp. The middle is a transition region and the bottom layer is 90% pulp and 10% synthetic pulp used as a binder. This is useful as an adult incontinence product in which the upper layer is in contact with the user's skin. One object of this product is to keep the absorbent pulp away from the user's skin.

A still further product may have an upper layer of 100% polyester, which is nonabsorbent and resilient. The middle layer may be a mixed blend of polyester and pulp, while the bottom layer is pulp and synthetic pulp, which is resilient and absorbent.

While the present invention has been particularly shown and described with reference to preferred embodiments thereof, it will be understood by those skilled in the art that various changes in form and details may be made therein without departing from the spirit and scope of the invention. In particular, when multiple sources are fed to a lickerin they need not each occupy 50% of the space. One may occupy more space than another and there may be gaps between them. Also other products may be created by sequentially feeding the products or halting the feeding for certain periods.

What is claimed is:

1. A method of forming a web of fibers comprising the steps of: feeding at least one source of fibrous material into engagement with one of two lickerins and feeding at least one other source of fibrous material of different composition into engagement with the other lickerin, said lickerins rotating toward each other about parallel axes such that the fibrous material is opened to form individualized fibers; doffing the fibers form the lickerins in the form of fiber streams;

directing the fiber streams toward each other and into a mixing zone;

selectively intercepting and redirecting at least part of each fiber stream within the mixing zone with at least two independently vertically movable baffle segments, each said baffle segment corresponding to a longitudinal segment along the operating length of said lickerins, at least one of said baffle segments being at a different vertical height;

receiving and accumulating the fiber streams on a conveying belt, after they have passed through the mixing zone, to form a web of material; and moving the conveying belt parallel to the axes of the lickerins.

2. A method of forming a web as claimed in claim 1, wherein two sources of fiber materials are fed to at least one of said lickerin by independent feeding means segments, each feeding means segment corresponding to one of said longitudinal segments of said lickerins.

3. A method of forming a web of fibers comprising the steps of:

feeding at least two sources of different fibrous material at independent separate speeds into independent engagement with one of two lickerins rotating toward each other about parallel axes and at least one source of fibrous material to the other lickerin, such that the fibrous material is opened to form individualized fibers, said feeding being performed by feed segments corresponding to longitudinal segments along the operating length of said at least one lickerin;

doffing the fibers from said lickerins in the form of fiber streams;

directing the fiber streams into a mixing zone;

selectively intercepting and redirecting at least part of each said fiber stream within said mixing zone with at least two independently vertically movable vertical baffles, at least one of said baffle segments being at a different vertical height;

receiving the fiber streams on a conveying belt, after they have passed through the mixing zone, in condensing zone located beyond the mixing zone;

moving the conveying belt parallel to the axes of the lickerins; and accumulating the fibers from the fiber streams on the conveying belt to form a web of material.

4. A method as claimed in claims 1 or 3, further comprising the step of spraying a powder onto the forming web by introducing the powder into said fiber stream.

5. A method of forming a cylindrical web of fibers comprising the steps of:

feeding a first source of fibrous material into engagement with a first lickerin;

feeding a second source of fibrous material into engagement with a second lickerin arranged with its axis parallel to the axis of said first lickerin;

rotating said first and second lickerins toward each other about their axes such that the fibrous material is opened so as to form individualized fibers;

doffing the fibers from the first and second lickerins in the form of two fiber streams directed toward each other and a mixing zone;

forming a foraminous flat conveying belt into a U-shape as it enters a condensing zone beyond the mixing zone in the direction of travel of the fiber streams;

intercepting the streams of fibers, after they have passed through the mixing zone, with the U-shaped conveying belt;

moving the conveying belt parallel to the axes of the lickerins;

accumulating the fibers from the fiber streams on the conveying belt to form a web of material;

guiding the U-shaped conveying belt into a cylindrical shape to form the cylindrical web;

fixing said cylindrical web in the cylindrical shape;

releasing the conveying belt back to a flat shape from said cylindrical shape; and separating the resulting cylindrical web product from the conveying belt.

6. A method as claimed in claim 5, wherein said accumulating step comprises the steps of:

selectively directing said fibers to predetermined zones on the inner surface of said U-shaped conveying belt by entraining said fibers in at least one air stream;

forming said air stream by a vacuum force created beyond the conveying belt; and varying the vacuum force from a minimum at the center of said conveying belt to a maximum at the edges of said belt during at least a portion of time the conveying belt is in the condensing zone.

7. A method as claimed in claim 6 further including the step of inserting at least one baffle into the mixing zone so as to at least partially block the fiber streams and vary the composition of the web.

8. A method of forming a fibrous structure as claimed in claim 5, wherein the step of feeding a first source of fibrous materials involves simultaneously feeding at least two different fibrous material with generally the same functional fiber length to different portions of the first lickerin.

9. A method of forming a fibrous structure according to claim 5, additionally comprising the step of depositing a powdered material onto the forming web.

* * * * *